United States Patent

Morimoto et al.

[11] Patent Number: 5,534,647
[45] Date of Patent: Jul. 9, 1996

[54] VINYL MONOMER HAVING LINEAR CARBONATE AND HYDROXYL GROUPS

[75] Inventors: Takao Morimoto, Suita; Shinji Nakano, Takatsuki, both of Japan

[73] Assignee: Nippon Paint Co., Ltd., Osaka, Japan

[21] Appl. No.: 466,684

[22] Filed: Jun. 6, 1995

[30] Foreign Application Priority Data

Jun. 16, 1994 [JP] Japan .................................. 6-159438

[51] Int. Cl.$^6$ .................................................. C07C 69/96
[52] U.S. Cl. ........................... 558/275; 558/273; 558/276
[58] Field of Search ..................... 558/276, 275, 558/273

[56] References Cited

U.S. PATENT DOCUMENTS 5,446,110  8/1995  Nakano et al. ......................... 525/439

OTHER PUBLICATIONS

Greene, T. W. *Protective Groups in Organic Synthesis*; John Wiley & Sons: New York, 1981; pp. 288–302.

*Primary Examiner*—Johann Richter
*Assistant Examiner*—Michael G. Ambrose
*Attorney, Agent, or Firm*—Millen, White, Zelano & Branigan

[57] ABSTRACT

For use as a monomer for producing hydroxyl group-containing vinyl polymers, there is provided a compound of the formula:

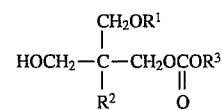

wherein $R^1$ is acryloyl, methacryloyl or 4-vinylbenzyl; $R^2$ is an alkyl; and $R^3$ is an alkyl, alkoxyalkyl, alkenyl, alkynyl, aralkyl or aryl.

4 Claims, No Drawings

VINYL MONOMER HAVING LINEAR CARBONATE AND HYDROXYL GROUPS

BACKGROUND OF THE INVENTION

Hydroxyl group-containing vinyl polymers such as hydroxyl group-containing acrylic polymers which may be crosslinked with an external crosslinker have been widely used in the coating industry as a vehicle resin of thermosetting coating compositions. Such polymers are conventionally produced by copolymerizing a hydroxyalkyl acrylate or methacrylate such as 2-hydroxyethyl methacrylate with other polymerizable monomers.

A need exists for a monomer which may be used as a comonomer for producing hydroxyl group-containing vinyl polymers.

BRIEF DESCRIPTION OF THE INVENTION

The present invention provides a new type of monomers and their production method for use as a comonomer in the manufacture of hydroxyl group-containing vinyl polymers. According to the present invention, there is provided a compound of the formula I;

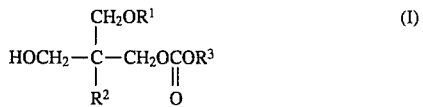

wherein $R^1$ is acryloyl, methacryloyl or 4-vinylbenzyl; $R^2$ is an alkyl of up to 4 carbon atoms; and $R^3$ is alkyl, alkoxyalkyl, alkenyl, alkynyl, aralkyl or aryl, all being of up to 18 carbon atoms.

In another aspect, the present provides a method for preparing the compound of the above formula I comprising reacting a cyclic carbonate of the formula II:

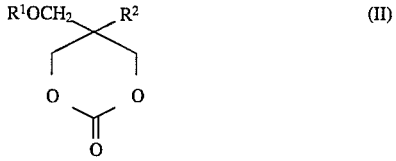

wherein $R^1$ and $R^2$ are as defined, with an alcohol of the formula III: $R^3OH$, wherein $R^3$ is as defined, in the presence of a catalyst.

DETAILED DESCRIPTION OF THE INVENTION

Part of the starting cyclic carbonates of the formula II ($R^1$=methacryloyl or 4-vinylbenzyl, $R^2$=ethyl) have been disclosed by Endo et al., in Polymer Preprints Japan, Vol. 42(2), 244 (1993). They are produced by reacting 5-ethyl-5-hydroxymethyl-2-oxo-1,3-dioxane with chloromethylstyrene or methacryloyl chloride. 5-Ethyl-5-hydroxymethyl-2-oxo-1,3-dioxane may be, in turn, produced by reacting trimethylpropane with phosgene. The cyclic carbonates of the formula II wherein $R^2$ is other than ethyl may be produced similarly by reacting the corresponding 5-alkyl-5-hydroxymethyl-2-oxo-1,3-dioxane with chloromethylstyrene or (meth)acryloyl chloride.

Alcohols of the formula III: $R^3OH$ which may be used in the synthesis of the compound of the formula I include alkanols such as methanol, ethanol, n-propanol, n-butanol, 2-ethylhexanol, stearyl alcohol, isopropanol or sec.butanol; glycol monoalkyl ethers such as ethylene glycol monobutyl ether; alkenyl alcohols such as crotyl alcohol; alkynyl alcohols such as propargyl alcohol; aralkyl alcohols such as benzyl alcohol; and phenols.

Catalysts which may be used in the reaction between the cyclic carbonates of the formula II and the alcohols of the formula III include organic or inorganic tin compounds such as dibutyltin oxide, dibutyltin dilaurate, dibutyltin dichloride, hydroxylbutyltin oxide, stannous chloride, stannous bromide or stannous iodide; tungsten compounds such as phosphotungstic acid or silicotungstic acid; Bronsted acids such as hydrogen fluoride, hydrogen chloride, hydrogen bromide, sulphuric acid, p-toluenesulfonic acid, dodecylbenzene sulfonic acid, methanesulfonic acid, trifluoroacetic acid or trifluoromethanesulfonic acid; strongly acidic ion exchange resins such as Amberlyst 15; and Brønsted acid anion salts of onium of nitrogen, sulfur, phosphorus or iodine. Typical examples of such onium salts are listed below:

(i) Quarternary ammonium salts:
N,N-dimethyl-N-benzylanilinium hexafluoroantimonate;
N,N-diethyl-N-benzylanilinium tetrafluoroborate;
N-benzylpyridinium hexafluoroantimonate;
N-benzylpyridinium triflate;
N-(4-methoxybenzyl)pyridinium hexafluoroantimonate;
N,N-diethyl-N-(4-methoxybenzyl)toluidinium hexafluoroantimonate; and
N,N-dimethyl-N-(4-methoxybenzyl)toluidinium hexafluoroantimonate.

(ii) Sulfonium salts:
triphenylsulfonium tetrafluoroborate;
triphenylsulfonium hexafluoroantimonate;
triphenylsulfonium hexafluoroarsenate;
ADEKA CP-66(Asahi Denka Kogyo K.K.);
ADEKA CP-77(Asahi Denka Kogyo K.K.);
tri-(4-methoxyphenyl)sulfonium hexafluoroantimonate; and
diphenyl-(4-phenylthiophenyl)sulfonium hexafluoroantimonate.

(iii) Phosphonium salts
ethyltriphenylphosphonium hexafluoroantimonate; and
tetrabutylphosphonium hexafluoroantimonate.

(iv) Iodonium salts:
diphenyliodonium hexafluoroantimonate;
di-4-chlorophenyliodonium hexafluoroantimonate;
di-p-tolyliodonium hexafluoroantimonate; and
phenyl-(4-methoxyphenyl)iodonium hexafluoroantimonate.

Anions of the above onium salts may be replaced by other Bronsted acid anions such as acetate, propionate, octanoate, laurate, stearate, benzoate, benzensulfonate, toluenesulfonate, dodecylbenzenesulfonate or perchlorate.

The amount of catalyst is preferably more than 0.01 mol % relative to the alcohol of formula III. The reaction may be performed in the absence or presence of an aprotic solvent. Examples of such solvents are aromatic hydrocarbons such as benzene or toluene; esters such as ethyl or butyl acetate; ketones such as acetone, methyl isobutyl ketone; halogenated hydrocarbons such as dichoromethane or dichloroethane, ethers such as tetrahydrofuran or dioxane; other aprotic solvents such as acetonitrile, nitrobenzene or nitromethane. Excessive alcohols of the formula III may also serve as a reaction solvent. The optimum reaction temperature will vary depending upon the nature of particular catalyst and reactants used and generally ranges between room temparature and 120° C.

EXAMPLES

The following examples are given for illustrative purposes only and not intended to limit the scope of the present invention thereto.

Example 1

2-Ethyl-2-methacryloyloxymethyl-3-methoxycarbonyloxypropanol 11.4 g of 5-ethyl-5-methacryloyloxymethyl-2-oxo-1,3-dioxane, 3.2 g of methanol and 0.285 g of p-toluenesulfonic acid were dissolved in 100 g of 1,2-dichloroethane. The solution was stirred for 2 hours at 40° C. and evaporated in vacuo to remove the solvent. After removing white precipitates by filtration, the residue was further concentrated whereupon the title compound was recovered as a colorless oil.

$^1$H-NMR; 0.79–0.83 (t,3H), 1.33–1.36 (q,2H), 1.87 (s,3H), 3.32 (s,2H), 3.66 (s,3H), 3.95 (s,2H), 4.01 (s, 2H), 4.74–4.75 (t,1H), 5.66 (s,1H), 6.02 (s,1H).

Example 2

2-Ethyl-2-(4-vinylbenzyloxy)methyl-3-ethoxycarbonyloxypropanol

Analogous to Example 1, the title compound was synthesized using 13.8 g of 5-ethyl-5-(4-vinylbenzyloxy) methyl-2-oxo-1,3-dioxane, 4,6 g of ethanol and 0.2 g of p-toluenesulfonic acid.

$^1$H-NMR; 0.79–0.83 (t,3H), 0.86–0.90 (t,3H), 1.33–1.36 (q,2H), 1.87 (q,2H), 3.32 (s,2H), 3.95 (s,2H) 4.02 (s,2H), 4.03–4.07 (t,2H), 4.41 (s,2H), 4.74–4.75 (t,1H), 5.14–5.18 (d,1H), 5.64–5.70 (d,1H), 6.61–6.70 (m,1H), 7.08–7.10 (d,2H), 7.26–7.29 (d,2H).

Example 3

2-Ethyl-2-methacryloyloxymethyl-3-butoxycarbonyloxypropanol

Analogous to Example 1, the title compound was synthesized using 22.8 g of 5-ethyl-5-methacryloyloxymethyl-2-oxo-1,3-dioxane, 37 g of butanol and 3 g of Amberlyst 15E.

$^1$H-NMR; 0.79–0.83 (t,3H), 0.86–0.90 (t,3H), 1.30–1.33 (m,2H), 1.33–1.36 (q,2H), 1.54–1.58 (m,2H), 1.87 (s,3H), 3.32 (s,2H), 3.95 (s,2H), 4.01 (s,2H), 4.03–4.07 (t,2H), 4.74–4.75 (t,1H), 5.66 (s,1H), 6.02 (s,1H).

Example 4

2-ethyl-2-methacryloyloxymethyl-3-ethoxycarbonyloxypropanol

Example 1 was followed to synthesize the title compound except that 4.6 g of ethanol was replaced for 3.2 g of methanol.

$^1$H-NMR; 0.79–0.83 (t,3H), 0.86–0.90 (t,3H), 1.33–1.36 (q,2H), 1.87 (s,3H), 3.32 (s,2H), 3.95 (s,2H), 4.02 (s,2H), 4.03–4.07 (t,2H), 4.74–4.75 (t,1H), 5.66 (s,1H), 6.02 (s,1H).

Example 5

2-Ethyl-2-methacryloylmethyl-3-benzyloxycarbonyloxypropanol

The title compound was synthesized using 22.8 g of 5-ethyl-5-methacryloyloxymethyl-2-oxo-1,3-dioxane, 32.4 g of benzyl alcohol and 0.1 g of p-toluenesulfonic acid.

$^1$H-NMR; 0.79–0.83 (t,3H), 1.33–1.36 (q,2H), 1.87 (s,3H), 3.31 (s,2H), 3.95 (s,2H), 4.02 (s,2H) 4.41 (s,2H), 4.74–4.75 (t,1H), 5.66 (s,1H), 6.02 (s,1H), 7.10–7.40 (m,5H).

Example 6

2-Ethyl-2-acryloyloxymethyl-3-butoxycarbonyloxypropanol

Example 3 was followed to synthesize the title compound except that 21.4 g of 5-ethyl-5-acryloyloxymethyl-2-oxo-1,3-dioxane was replaced for 22.8 g of 5-ethyl-5-methacryloyloxymethyl- 2-oxo-1,3-dioxane.

$^1$H-NMR; 0.79–0.83 (t,3H), 0.86–0.90 (t,3H), 1.30–1.33 (m,2H), 1.33–1.36 (q,2H), 1.54–1.58 (m,2H), 3.32 (s,2H), 3.95 (s,2H), 4.01 (s,2H), 4.03–4.07 (t,2H), 4.74–4.75 (t,1H), 5.80–5.84 (m,1H), 6.07–6.17 (m,1H), 6.38–6.42 (m,1H).

Example 7

2-Ethyl-2-acryloyloxymethyl-3-methoxycarbonyloxypropanol

Analogous to Example 1, the title compound was synthesized using 21.4 g of 5-ethyl-5-acryloyloxymethyl-2 -oxo-1,3-dioxane, 96 g of methanol and 0.1 g of p-toluenesulfonic acid.

$^1$H-NMR; 0.79–0.83 (t,3H), 1.33–1.36 (q,2H), 3.32 (s,2H), 3.66 (s,3H), 3.96 (s,2H), 4.01 (s,2H), 4.74–4.75 (t,1H), 5.80–5.84 (m,1H), 6.07–6.17 (m, 1H), 6.38–6.42 (m,1H).

Example 8

2-Ethyl-2-methacryloyloxymethyl-3-propoxycarbonyloxypropanol

Example 3 was followed to synthesize the title compound except that 30 g of propanol was replaced for 37 g of butanol.

$^1$H-NMR; 0.79–0.83 (t,3H), 0.86–0.90 (t,3H), 1.33–1.36 (q,2H), 1.54–1.58 (m,2H), 1.87 (s,3H), 3.32 (s, 2H), 3.95 (s,2H), 4.01 (s,2H), 4.03–4.07 (t,2H), 4.74–4.75 (t,1H), 5.66 (s,1H), 6.02 (s,1H).

We claim:

1. A compound of the formula:

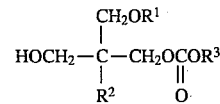

wherein $R^1$ is acryloyl, methacryloyl or 4-vinylbenzyl; $R^2$ is $C_{1-4}$-alkyl; and $R^3$ is alkyl, alkoxyalkyl, alkenyl, alkynyl, aralkyl or aryl, all being of up to 18 carbon atoms.

2. The compound of claim 1 wherein $R^1$ is acryloyl or methacryloyl, $R^2$ and $R^3$ are independently $C_{1-4}$-alkyl.

3. The compound of claim 1 which is 2-ethyl-2-methacryloyloxymethyl- 3-methoxycarbonyloxypropanol.

4. The compound of claim 1 which is 2-ethyl-2-(4-vinylbenzyloxy)methyl- 3-methoxycarbonyloxypropanol.

* * * * *